United States Patent [19]
Mentzer et al.

[11] Patent Number: 6,026,861
[45] Date of Patent: *Feb. 22, 2000

[54] METHOD FOR RE-INSULATING INSTALLED STEAM PIPE IN SITU

[75] Inventors: H Timothy Mentzer, Mt. Laurel; Leif Berquist, Englishtown, both of N.J.

[73] Assignee: Trigen Energy Corp., White Plains, N.Y.

[*] Notice: This patent is subject to a terminal disclaimer.

[21] Appl. No.: 09/050,298

[22] Filed: Mar. 30, 1998

Related U.S. Application Data

[62] Division of application No. 08/674,109, Jul. 1, 1996, Pat. No. 5,732,742.

[51] Int. Cl.[7] .................................................. F16L 55/18
[52] U.S. Cl. ........................... 138/97; 138/149; 264/36; 264/46.5; 156/94
[58] Field of Search ............................... 138/97, 98, 148, 138/149; 156/94, 74; 264/36, 46.4, 46.5, 46.6

[56] References Cited

U.S. PATENT DOCUMENTS

| | | | |
|---|---|---|---|
| 3,616,516 | 11/1971 | Corriston | 29/401 |
| 4,049,480 | 9/1977 | Kutschke | 156/94 |
| 4,219,050 | 8/1980 | Hargrave et al. | 138/97 |
| 4,698,877 | 10/1987 | Patell et al. | 29/157 R |
| 5,017,314 | 5/1991 | Zemanek et al. | 264/35 |
| 5,027,862 | 7/1991 | Laybourn | 138/99 |
| 5,125,147 | 6/1992 | Hickham | 29/402.09 |
| 5,194,193 | 3/1993 | Humphreys et al. | 264/35 |
| 5,241,993 | 9/1993 | Stephens | 138/98 |
| 5,427,154 | 6/1995 | Stephens | 138/98 |
| 5,560,395 | 10/1996 | Bissonnette et al. | 138/98 |

*Primary Examiner*—Patrick Brinson
*Attorney, Agent, or Firm*—Jay H. Maioli

[57] ABSTRACT

A method and apparatus for re-insulating underground steam pipe in situ includes the steps of creating at least one hole in the ground, inserting a liner into the hole, using a drill string to drill a hole in the conduit, inserting a tubing into the liner so that a first end of the tubing is positioned next to the pipe and a second end of the tubing is attached to a pumping system. The foam is then pumped through the tubing around the pipe and then the tubing is removed and the foam is allowed to cure and become rigid, thereby functioning as insulation.

The plastic foam may be a polyisocyanurate or a urethane-modified polyisocyanurate.

8 Claims, 14 Drawing Sheets

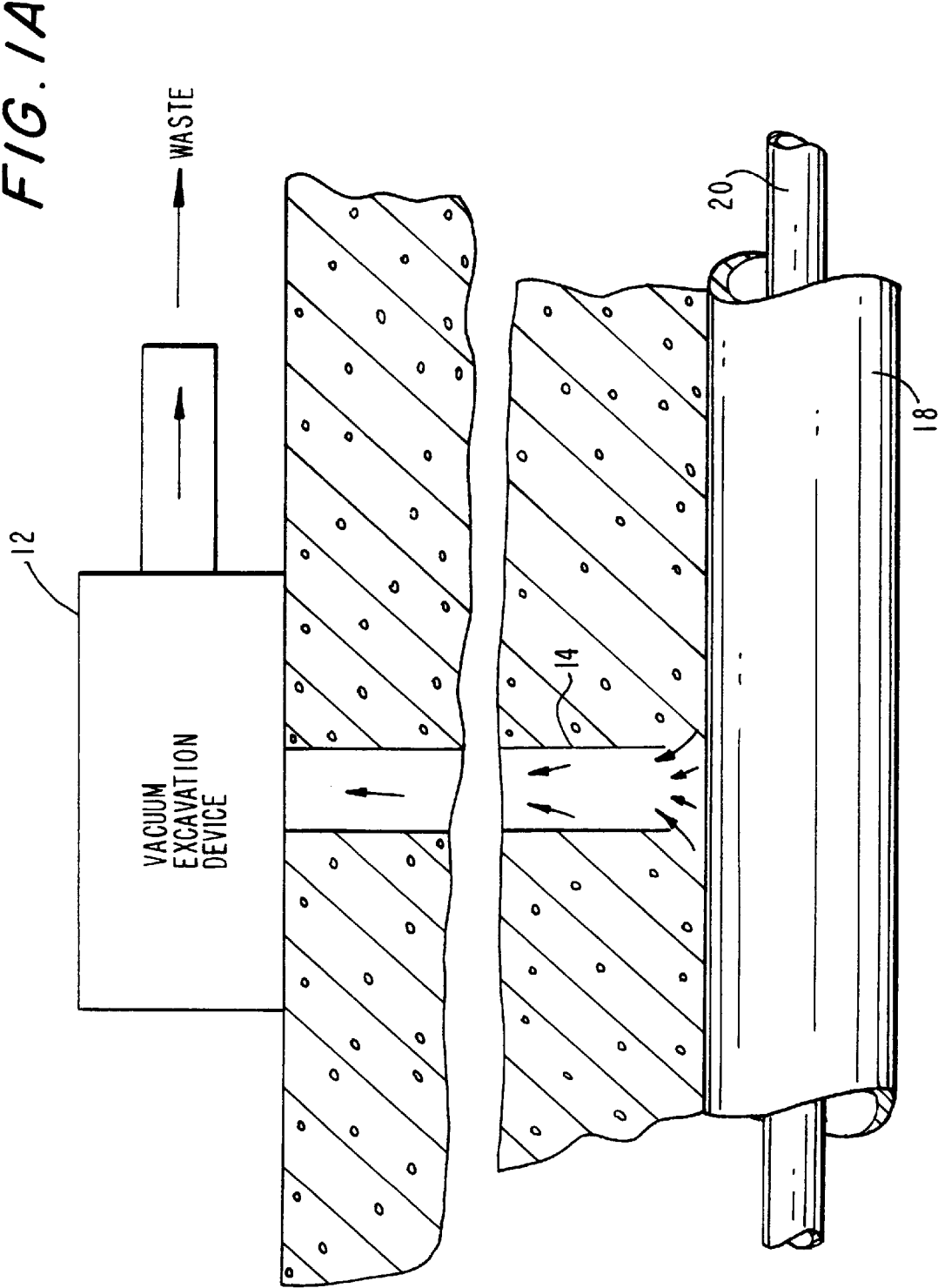

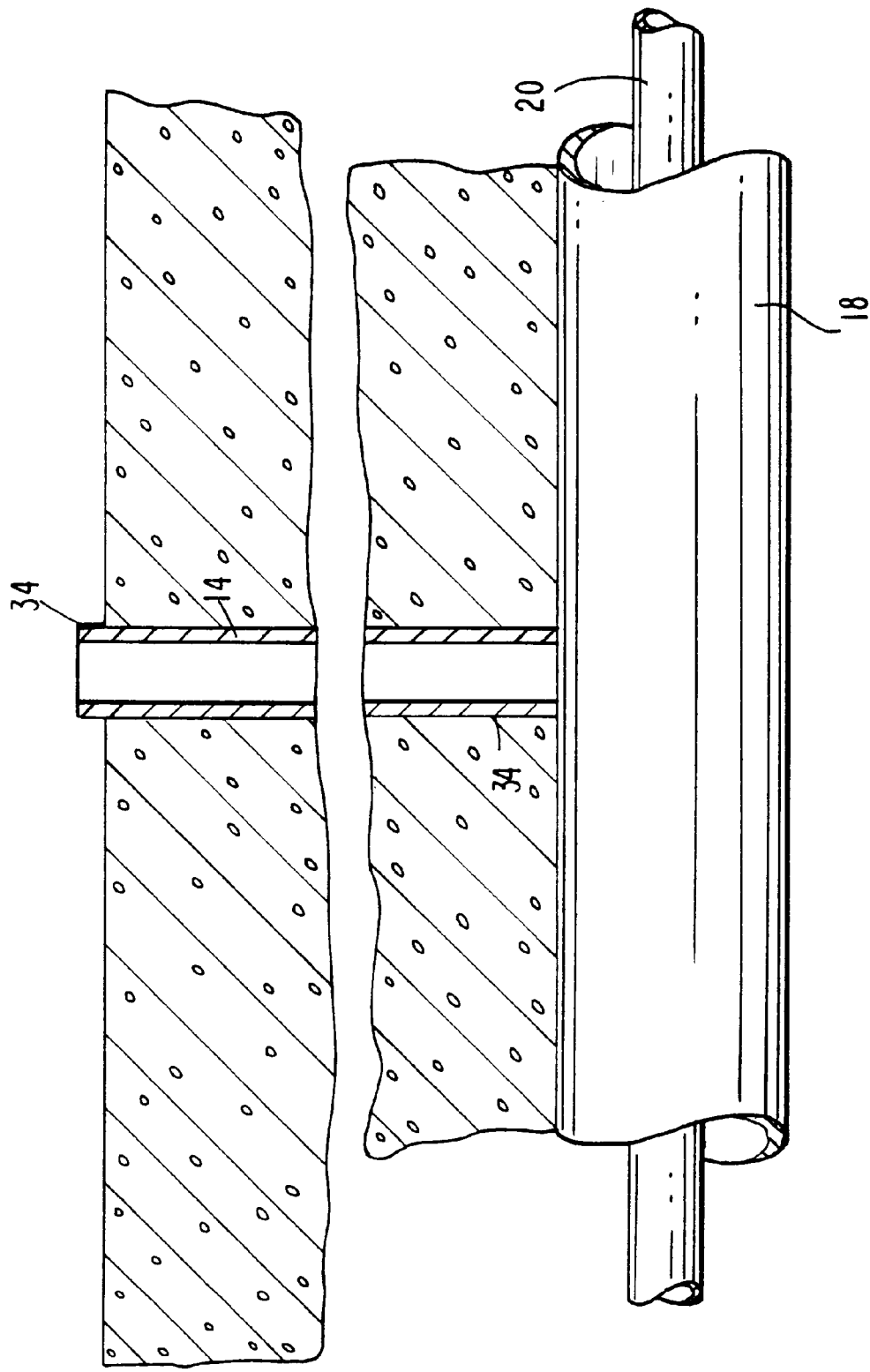

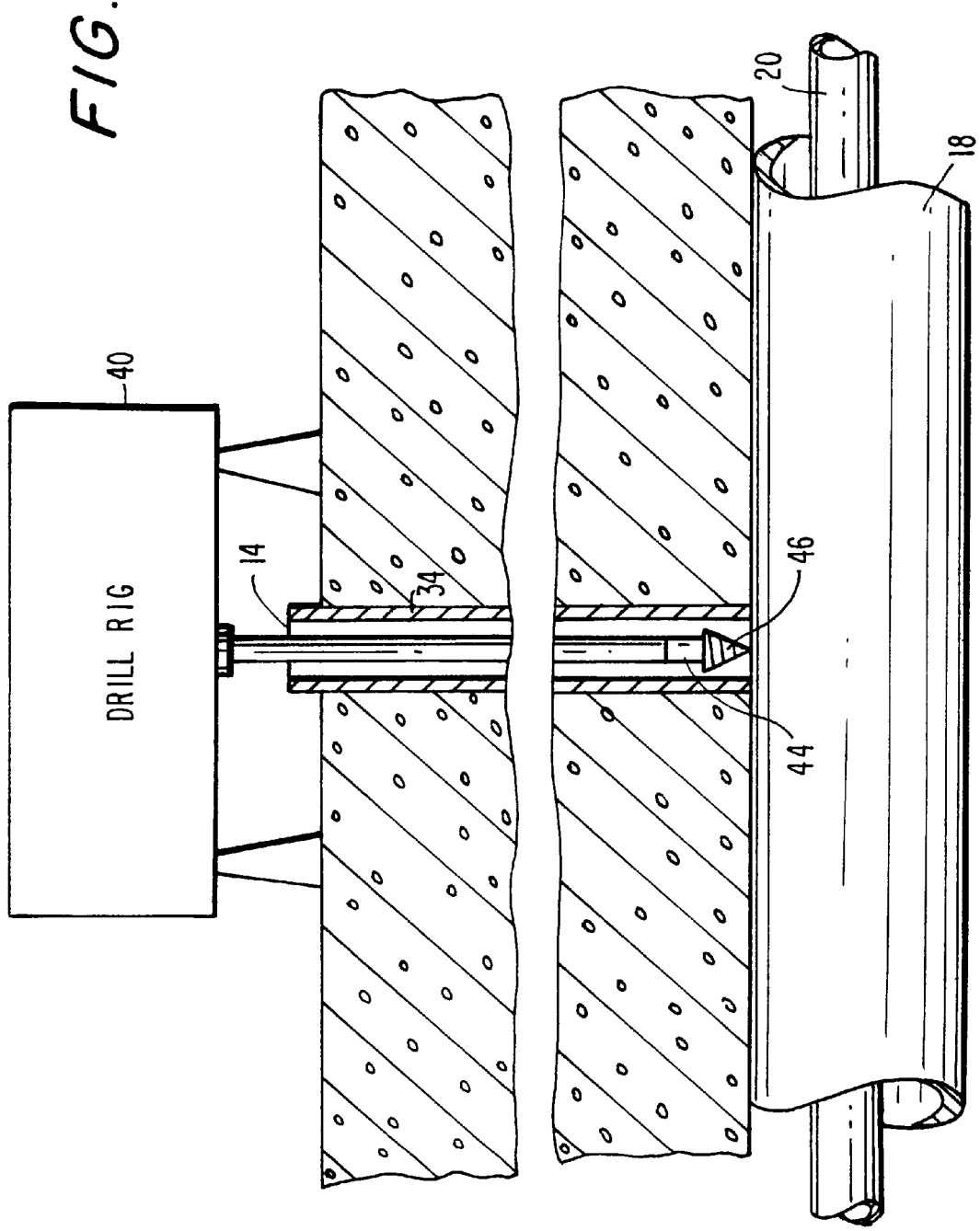

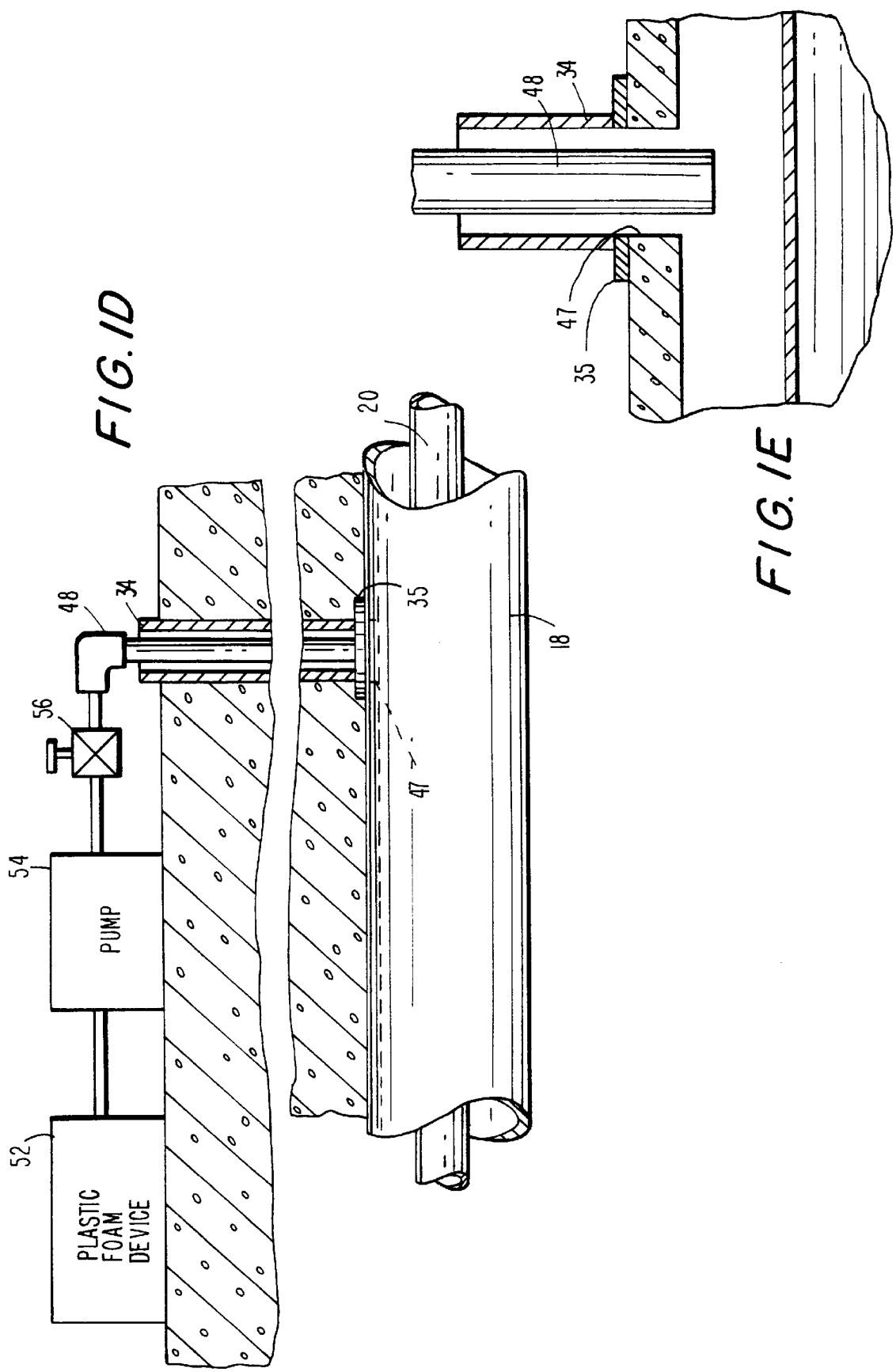

METHOD FOR RE-INSULATING INSTALLED STEAM PIPE IN SITU

This is a division of prior application Ser. No. 08/674,109 filed Jul. 1, 1996, now U.S. Pat No. 5,732,742.

This invention relates generally to a method for insulating steam pipe and, more particularly, to a method for re-insulating installed underground steam pipe and for performing the insulating process underground.

BACKGROUND OF THE INVENTION

Underground steam pipe systems are very necessary in most cities. These systems provide heat and energy to commercial and residential spaces alike. The pipe through which the steam flows can range anywhere from two to twenty-four inches in diameter and is typically made of steel. When steam passes through the steel pipe, the temperature of the pipe rises to 350°–450° F. Because metal is a good conductor of heat, a significant amount of heat would be expected to be dissipated or lost through the pipe, resulting in inefficiency. Therefore, in order to reduce heat dissipation, steel steam pipe is insulated when it is installed.

Foamed plastics are often used, for insulation purposes, at temperatures of up to 120° C., because of their low density, low thermal conductivity and resistance to moisture. Foamed polyurethane, for example, has an aged thermal conductivity of 0.016 W/m·K at 23° C. Other foamed plastics include polystyrene, polyvinyl chloride (PVC), and phenolic foams. These foamed plastics are "cured" or "cast" and are transformed into rigid structures. Objects of various shapes can be made simply by casting the foam inside a mold which is shaped to make the desired article. For steam pipe insulation applications, foamed plastics are transformed or "precast" into rigid half-cylinders or blocks. These half-cylinders are inserted into the annular area between the steel steam pipe and concrete or tile conduit. According to current practice, this process must necessarily be done before or during laying the pipe underground.

After a period of time and from constant exposure to high temperature, the insulation degrades and deteriorates. When this happens, insulating properties are lost and heat is dissipated through the steel pipe. Therefore, it becomes necessary to repair or reinsulate the pipe to return the steam system to its proper efficiency.

At present, there are a large number of underground steam pipe systems that were installed fifty to sixty years ago. Typically, this steam pipe was insulated when it was installed. For example, the metal pipe was laid inside of either concrete or tile conduit pipe. As further insulation, rigid plastic foam was fit in the two to six inch wide annular space between the steel pipe and the conduit pipe. After the forty to fifty years of continuous use that these steam systems have endured, the original insulation has either disintegrated or has become severely reduced in effective thickness to provide the thermal insulation that is required. Without insulation, a steam line at 350° to 450° F. will lose heat as the steam travels from the plant to the customer. This loss in heat results in the formation of condensate (water) that is then removed from the system through low drain points and steam traps located throughout the system. The efficiency loss due to the excessive condensate formation results in increased costs due to the fuel costs and the loss of chemicals added to the water at the plant making steam.

Also, over the course of fifty years or so, the original insulation decomposes from heat and age; the conduit cracks; ground water removes the original insulation and retrofitting becomes necessary. Thus, there is a need for a cost efficient method to retrofit existing underground steam pipe with new insulation.

Excavation, opening up the conduit, removing and replacing the insulation, while expensive, is generally the only procedure that produces acceptable results. Moreover, re-insulating the underground steam pipe entails numerous problems. First, the ground above the pipe must be removed in order to permit access to the pipe. This involves destroying sidewalks, roads and other structures that are costly to repair or replace after the work is completed. Second, the concrete conduit must be destroyed and replaced with new conduit. The pipes themselves must be removed in order to be retrofitted with new rigid foam insulation. Finally, the pipe must be repositioned underground. The current method is time-consuming as only short sections of pipe can be worked on at a time. As will be appreciated, the complete procedure requires a great expense in materials and labor, not to mention the cost and inconvenience caused by lack of service while the procedure is underway, since it is necessary to shut down the system. Even once the system is shut down, it can take an additional several days to cool sufficiently. Some companies have tried retrofitting with cementations boiler refractory material, but found the material too costly and lacking in performance. Until now, there was no alternative but to accept the heat loss and resulting additional cost.

OBJECTS AND SUMMARY OF THE INVENTION

Accordingly, it is an object of the present invention to provide a method and apparatus for insulating underground, metal steam pipe in situ that can overcome the problems inherent in previous systems.

According to one aspect of the present invention, a new and useful process technology is provided for the cost efficient insulation of underground steam pipe in which insulating foam is deposited around installed steam pipe. In another aspect, the invention comprises pumping uncured plastic foam into the annular space between installed underground steam pipe and surrounding insulation conduit and subsequently causing the foam to cure and become rigid.

In a still further aspect, the method for in-place insulation of an underground steam pipe comprises creating at least one hole in the ground, inserting tubing into the hole so that a first end of the tubing is positioned next to the pipe and a second end of the tubing is attached to a pumping system. The foam is then pumped through the tubing around the pipe and then the tubing is removed and the foam is allowed to cure and become rigid, thereby functioning as insulation.

The new insulation performs up to a temperature of 450° F. Moreover, the inventive process has the advantages of not requiring the digging up of existing pipe. The inventive process also has the advantage of eliminating the cost of purchasing and installing new conduit and pre-cast rigid foam insulation material. In addition to the cost savings from the process itself, another advantage of the present invention is that the steam transmission system does not have to be shut down during the re-insulation process. A further advantage of the invention is that it can be practiced year round. Yet another advantage of the invention is that up to 1,000 feet of pipe can be insulated or re-insulated at a time. This is because the inventive method provides the option of preparing multiple holes in advance and sequentially injecting the plastic foam into the multiple holes along up to 1,000 feet of conduit. Thus, the inventive method is highly time efficient.

Moreover, according to the present invention, the foam used is flowable, thus, it can more uniformly fill the area between the pipe and conduit and insulate more efficiently as compared to the previously proposed methods. Any remaining original insulation does not have to be removed, rather it can remain in place and the new foam is pumped around it. When the new foam cures, the old insulation becomes part of the new rigid foam structure.

Generally, the plastic insulating foam is a polyurethane. Other newer types of plastic foams such as polyisocyanurates, polystyrene, PVC and phenolic foams can be used in practicing the invention. In particular, recently developed urethane-modified rigid polyisocyanurate foams exhibit superior thermal stability and combustibility characteristics. Polyurethane-processing equipment can be used.

BRIEF DESCRIPTION OF THE DRAWINGS

FIG. 1A is an elevational view showing forming the hole for accessing the conduit according to an embodiment of the present invention.

FIG. 1B is an elevational view showing inserting the liner into the hole according to the embodiment of the present invention.

FIG. 1C is an elevational view showing drilling an insulation insertion hole according to the embodiment of the present invention.

FIG. 1D is an elevational view showing injecting the foam insulation according to the embodiment of the present invention.

Figure 3:
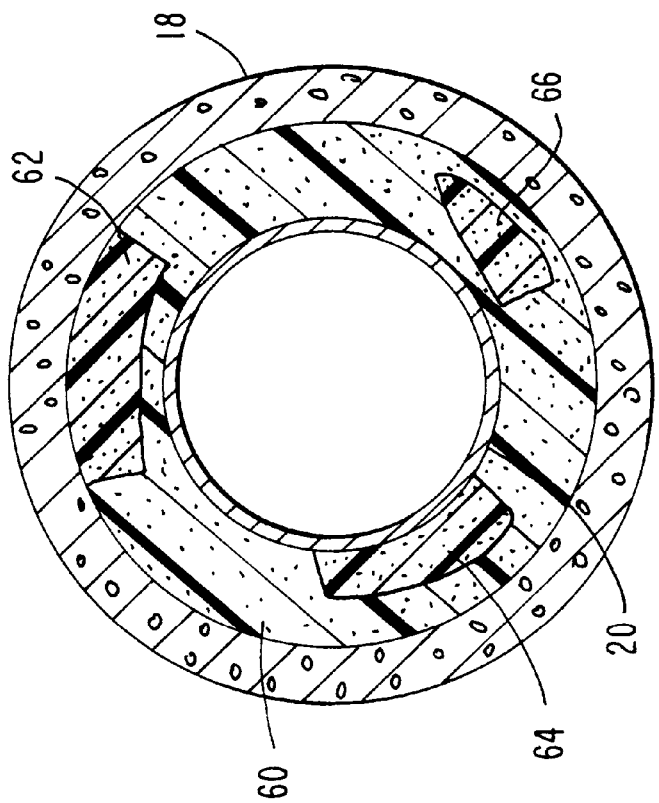
FIG. 3 is a cross-sectional view of the conduit, pipe, and annular area therebetween with the foamed insulation and portions of the old insulation present.

Table 1 shows a typical polyurethane foam formulation.

Table 2 shows a typical polyisocyanurate foam formulation.

DETAILED DESCRIPTION OF PREFERRED EMBODIMENTS

The plastic insulating foam may consist of two or three components which must be mixed before pumping. For example, a polyurethane foam may have one component which is an isocyanate and one component which is an amine. These two components must be mixed together before pumping. A typical polyurethane foam formulation is shown in Table 1. A typical polyisocyanurate foam formulation is shown in Table 2.

A preferred embodiment of the present invention wherein the steam pipe is encased in conduit and has an annular space between the pipe and the conduit provides for the following steps: creating at least one hole in the ground; lowering a drill into the hole; drilling a hole in the conduit; inserting tubing into the hole in the conduit so that a first end of the tubing is positioned next to the pipe and a second end of the tubing is attached to a pumping means; pumping the foam through the tubing so that the foam fills the annular space around the pipe; removing the tubing; and allowing the foam to cure and become rigid thereby functioning as insulation. Further, a plastic casing or liner of about twelve inches in diameter may be inserted into the hole before drilling the hole in the conduit.

First, as shown in FIG. 1A, a vacuum excavation truck or device 12 is used to suck a sixteen-inch diameter hole 14 or holes through the earth above the conduit 18 and steam pipe 20. Since only a relatively small hole is required, the disruption to the surface is minimal.

Next, as shown in FIG. 1B, PVC tubing, casing or liner of twelve inch diameter 34 is inserted into the hole or holes through which a drill will be lowered. Typically, the bottom end of the casing can have a flexible flange 35 (FIG. 1-E) formed thereon, not shown in FIG. 1B, so that a relatively tight seal can be obtained between the casing 34 and the exterior surface of the cement conduit 18. A drill is then lowered through the PVC tubing 34 and a four inch hole is drilled in the conduit as follows: First, a hole is drilled into the cement or tile conduit so that the annular space between the inside of the conduit 18 and the outside of the steel steampipe 20 can be accessed. This operation is represented in FIG. 1C in which any sort of suitable drilling apparatus or drill rig 40 is employed with a drill string 44 such as the kind used in drilling water wells and the like. At the end of the drill string 44 is a suitable rock bit 46 that must be sufficiently robust to drill through the cement conduit 18. In addition, care must be exercised, when drilling, that the drill does not damage the steel steampipe 20. This means that the drilling operation must be closely monitored and, in that regard, the exact depth of the conduit 18 and steampipe 20 will be generally known so that it is not a serious problem in simply drilling through the cement casing 18. In addition, another technique in making certain that the steel steampipe 20 is not damaged is to monitor the force being applied to the drill 44 so that the moment it pierces the cement conduit 18, the drilling operation may stop.

The present invention contemplates drilling a number of holes 47 along the length of the cement conduit 18, so that the operation of injecting the insulating foam over the length of the steel steam pipe can be performed as a series of closely timed operations. Two of these several holes are represented in FIG. 1-C. Once the hole 47 is formed in the cement conduit 18, fluorocarbon tubing measuring ¾ inch in diameter 48 is inserted through the hole in the conduit. It may take up to several days to insert the tubing in the case where several holes 47 have been formed in the cement conduit. The fluorocarbon tubing, 48 may then be capped or sealed with a suitable plug until the time for pumping. Then, if several holes in the conduit have been formed, all of the holes will be pumped on the same day.

In that regard, FIG. 1D represents the actual operation of injecting the insulating foam into the annular space between the cement conduit 18 and the steel steampipe 20. A suitable supply of the foam is provided shown generally at 52 and the plastic foam is then pumped by a suitable pump 54 through a metering valve 56 and then into the tube 48 that extends down through the casing 34 and into the annular space between the inside of the cement conduit 18 and the steel steampipe 20. The pumping system comprises a polyurethane pump that mixes and pumps the plastic foam through the fluorocarbon tubing 48. The new plastic foam insulation material is pumped through the fluorocarbon tubing 48 at a rate of 10–20 feet per minute. The new foam insulation is pumped a distance A (FIG. 1-C) that is not more than 100 feet into position. Less than optimal results are obtained if the distance pumped is greater than 100 feet.

Figure 2:
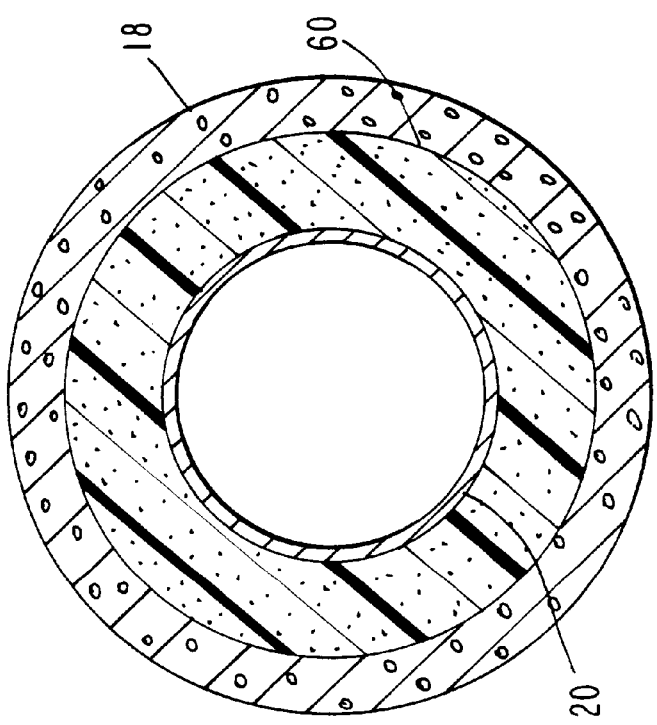
FIG. 2 is a cross-sectional view of the conduit, pipe and annular area therebetween following injecting the foam as shown in FIG. 1D.
Figure 4:
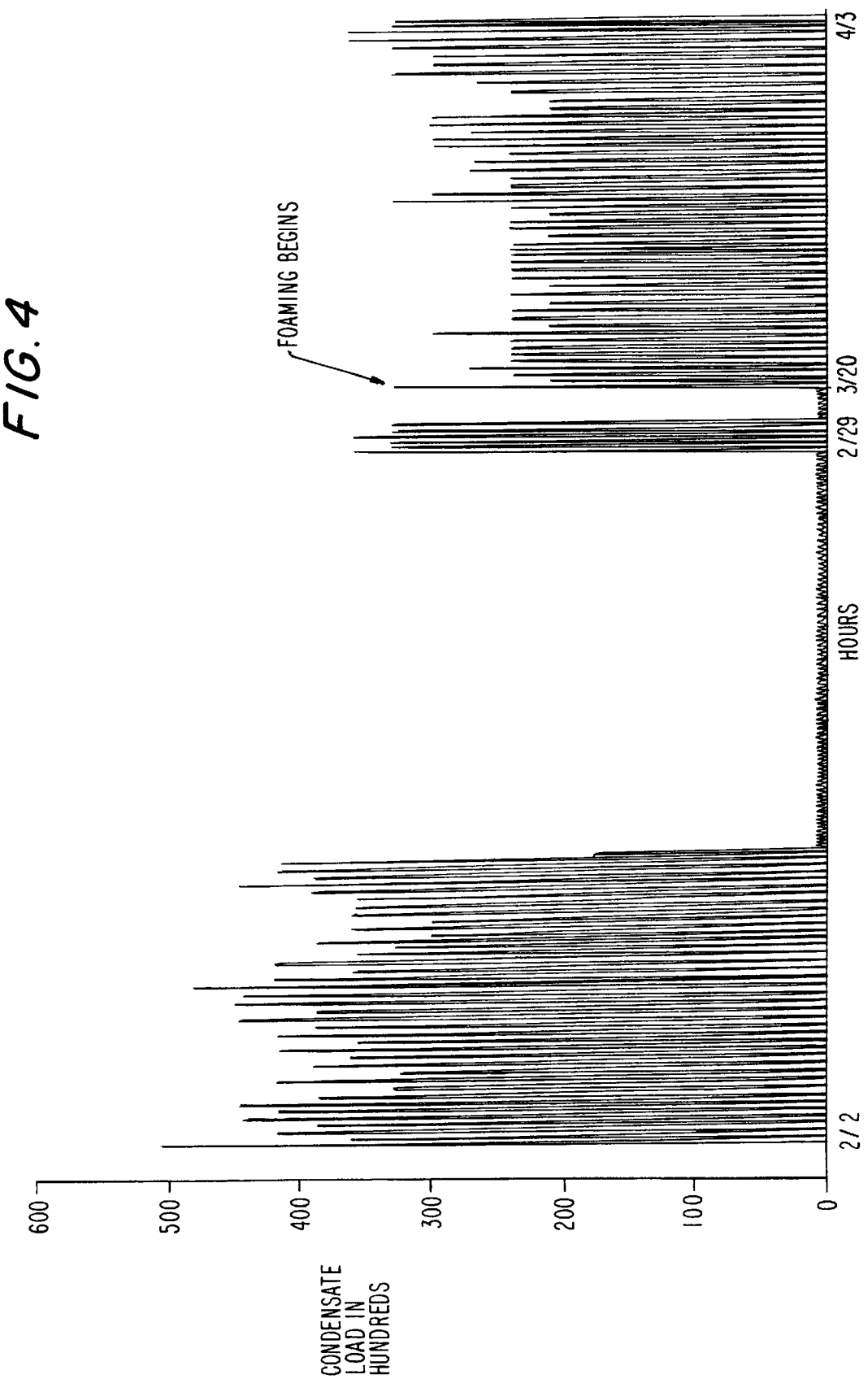
FIG. 4, FIG. 5 and FIG. 6 are graphs showing results data from in situ insulation of a 2,000 foot test section of buried piping as measured at Meter 1.
Figure 5:
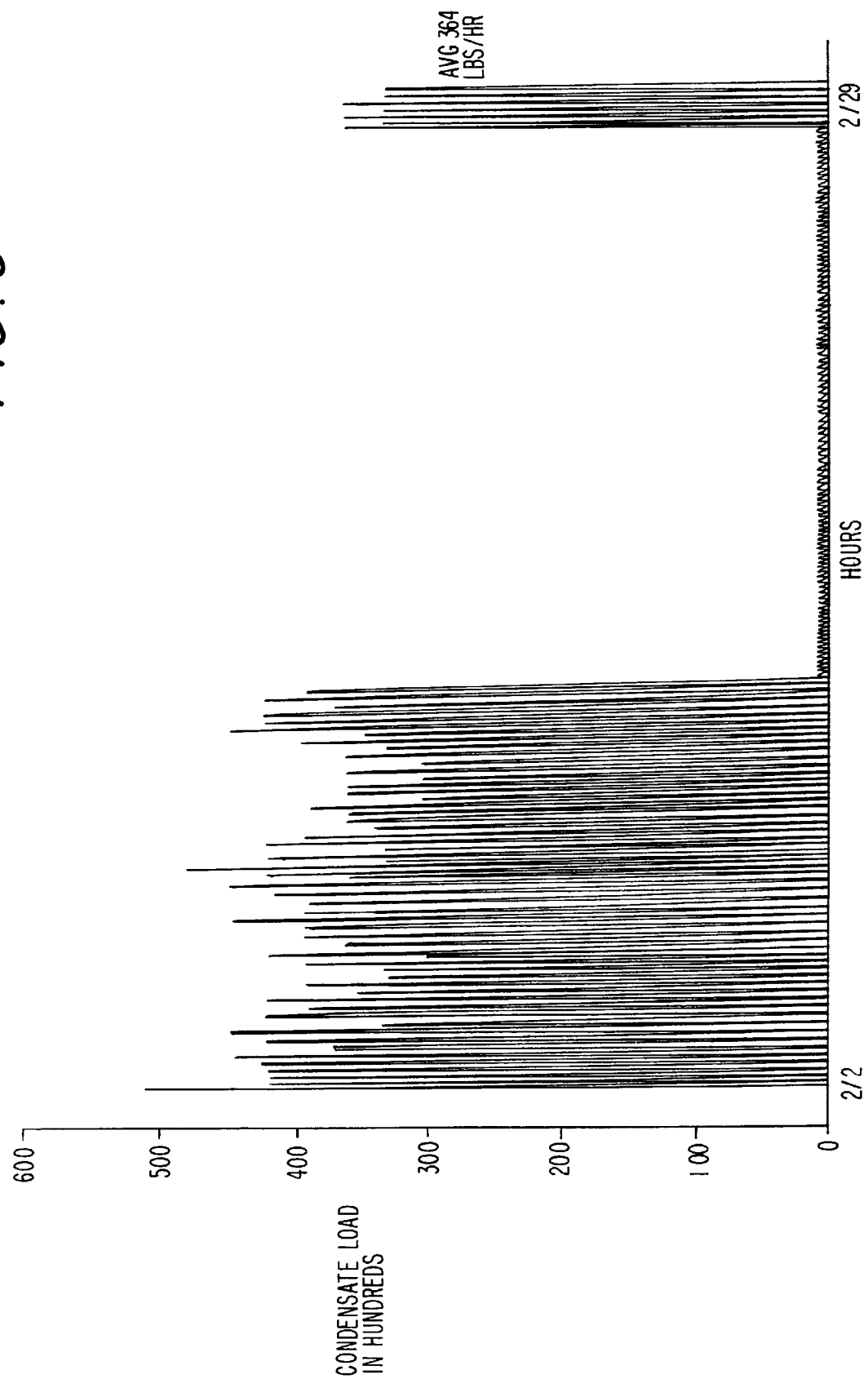
Figure 6:
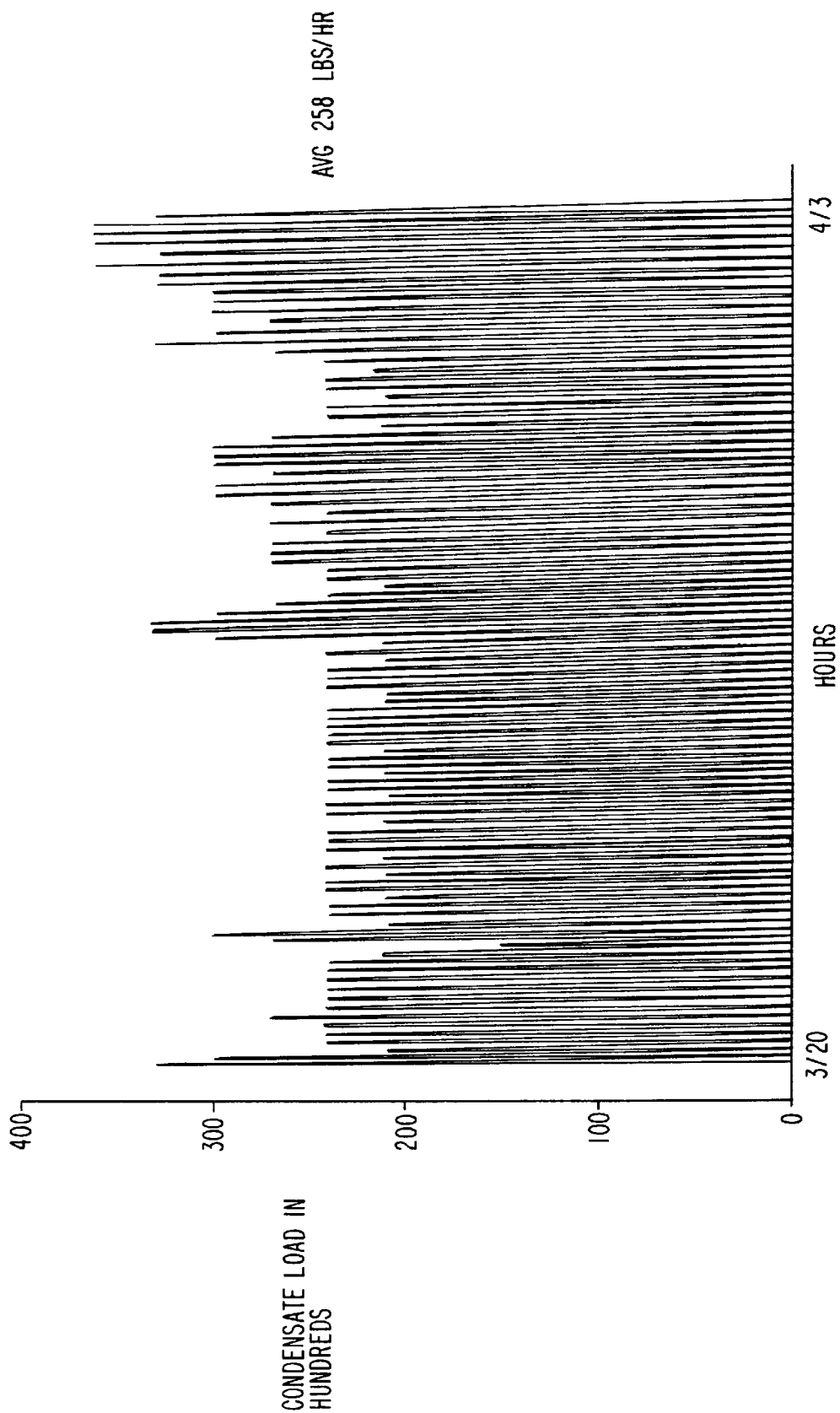
Figure 7:
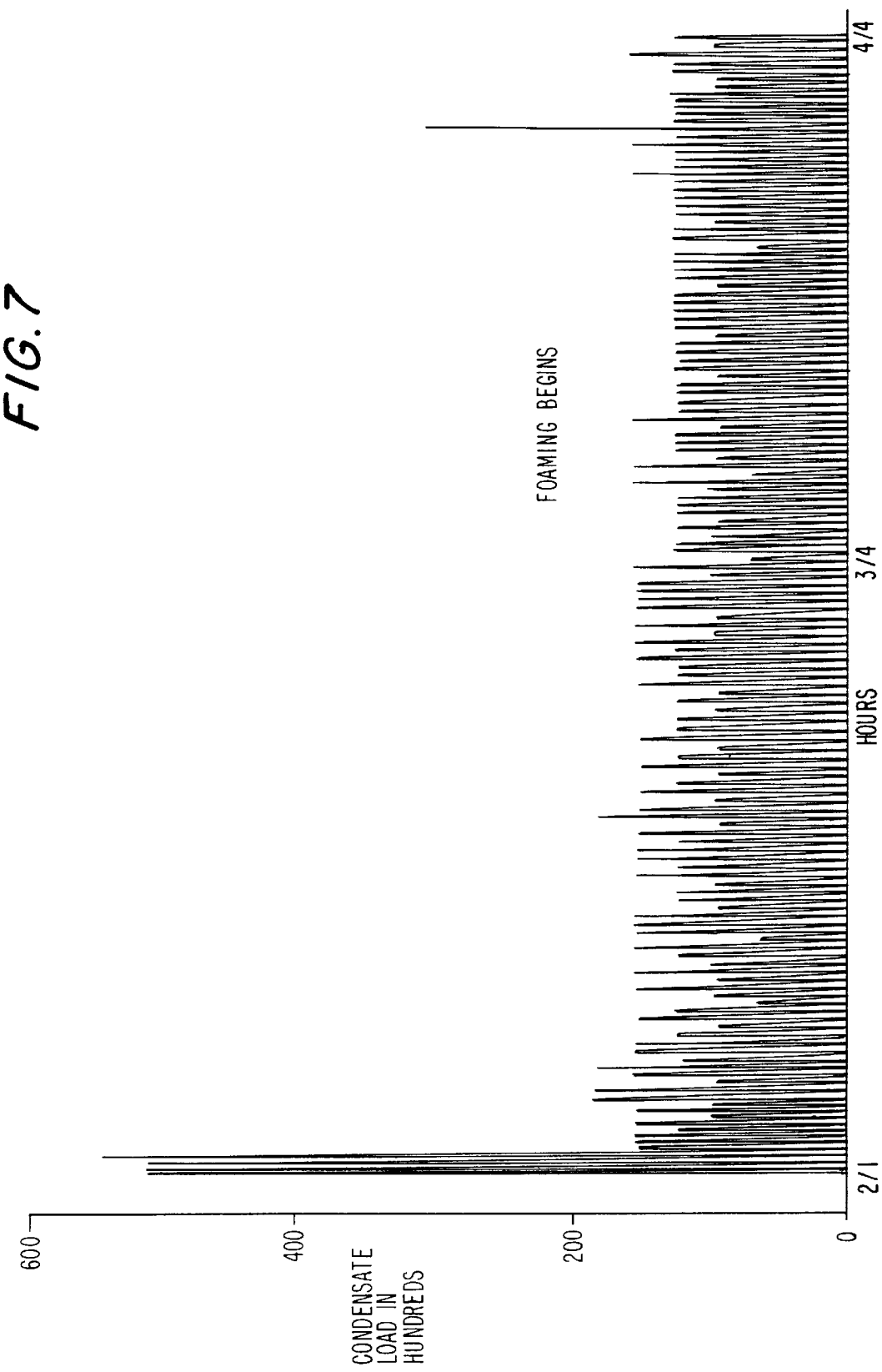
FIG. 7, FIG. 8 and FIG. 9 are graphs showing results data from in situ insulation of a 2,000 foot test section of buried piping as measured at Meter 2.
Figure 8:
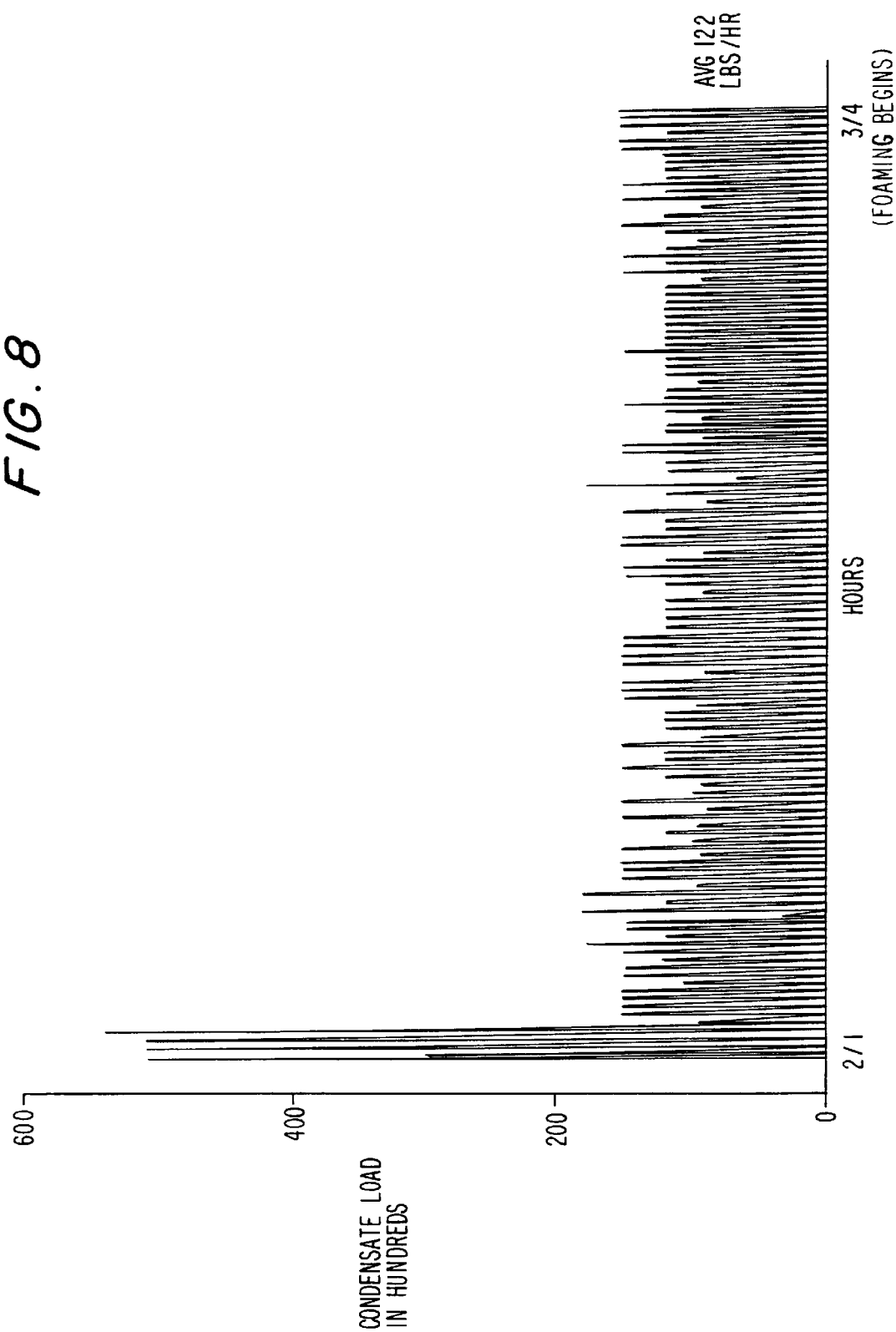
Figure 9:
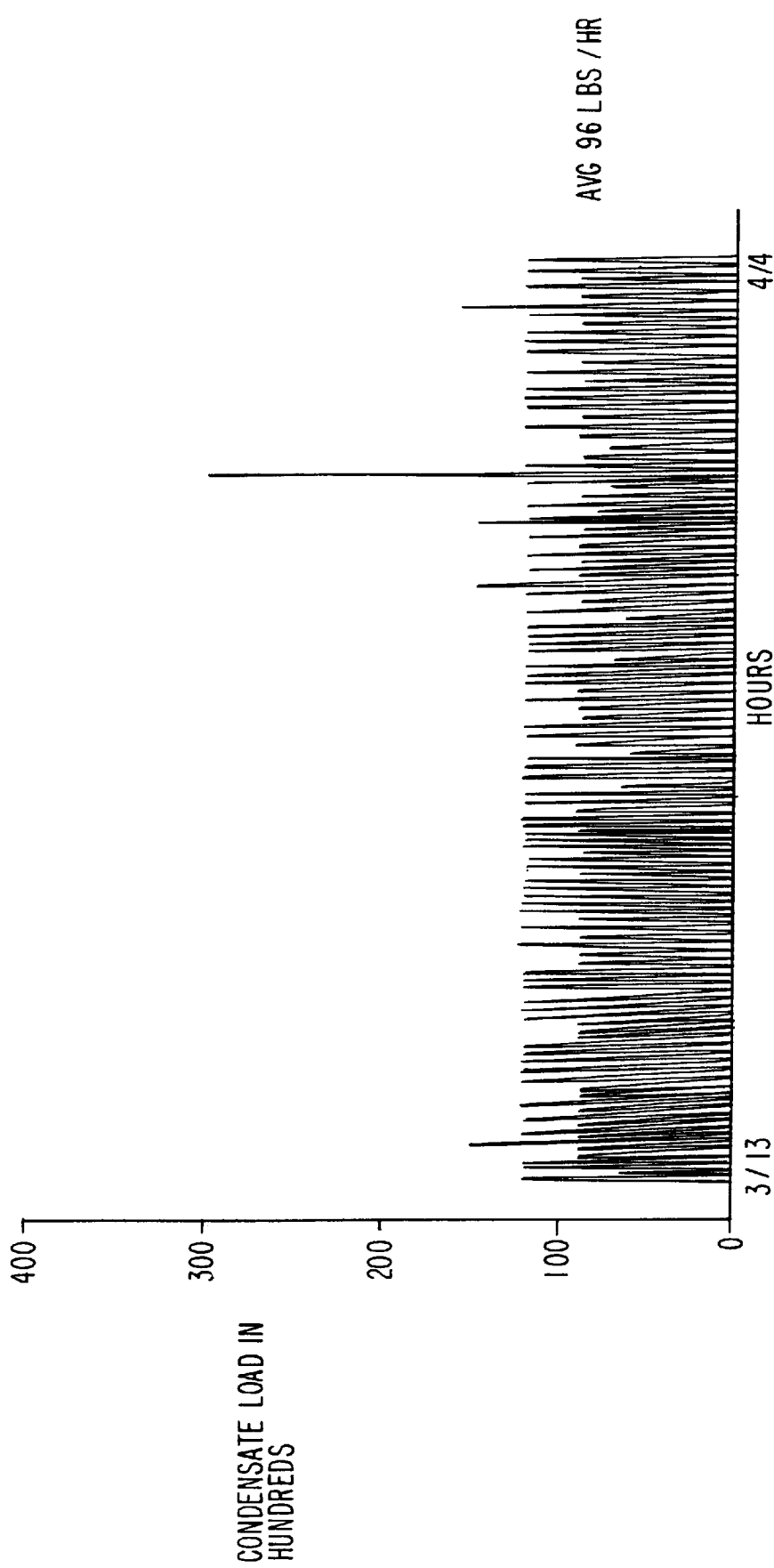
Figure 10:
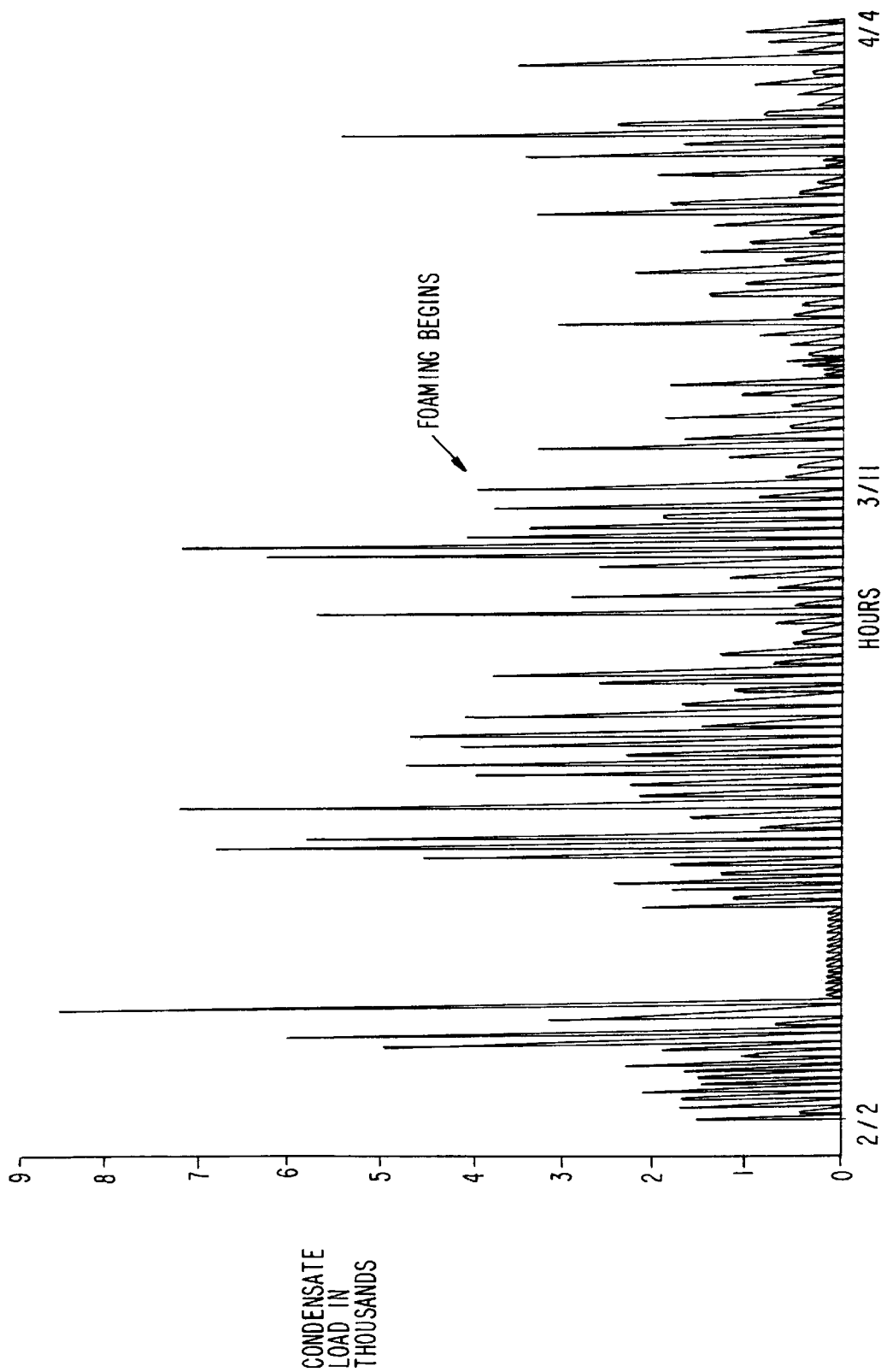
FIG. 10, FIG. 11 and FIG. 12 are graphs showing results data from in situ insulation of a 2,000 foot test section of buried piping as measured at Meter 3.
Figure 11:
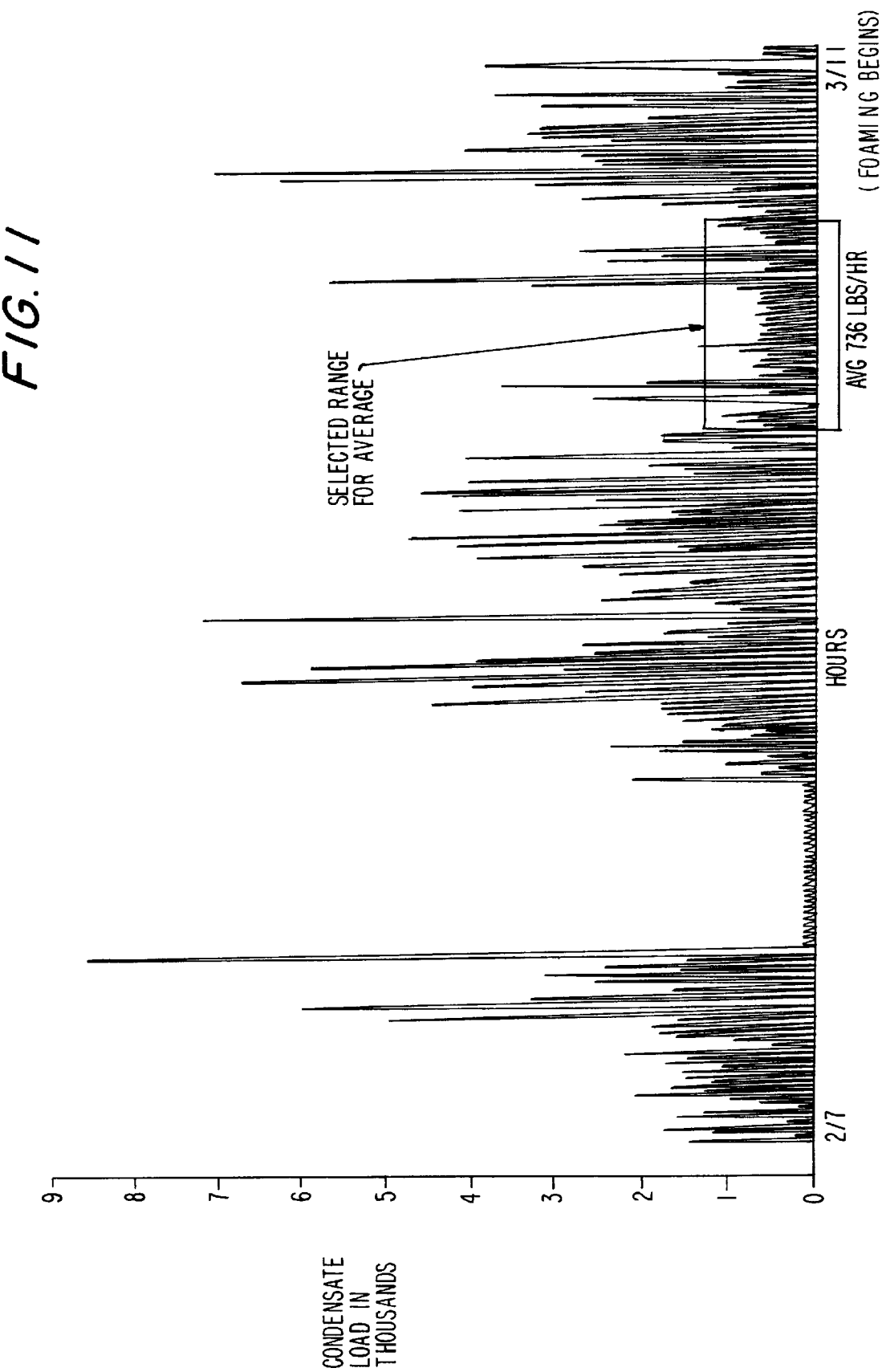
Figure 12:
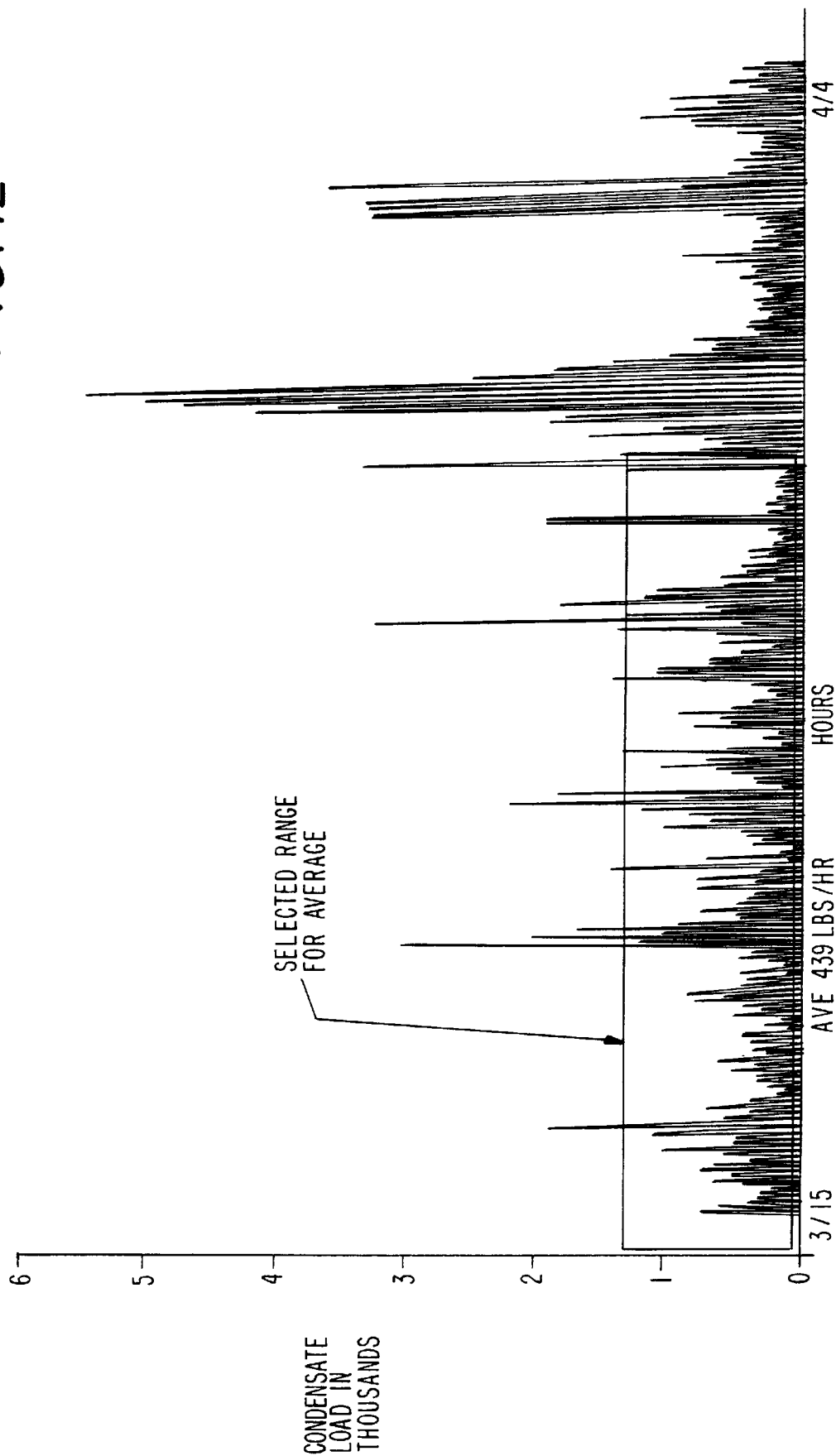

FIG. 2 is a cross-sectional view of the cement conduit 18 with the steel steampipe 20 arranged therein after the foam insulation injection operation has taken place. Thus, the annular space surrounding the steel steampipe 20 is completely filled with the new insulating foam structure 60 without requiring removal of the steampipe or the casing. Moreover, because the insulating foam expands upon injection, it completely fills the annular space. In addition, because the plastic foam will harden into a tough water resilient seal, it is not necessary to plug the hole 47 that was drilled into the cement conduit 18. All that is required is the removal of the PVC liner 34.

As described hereinabove, a further feature of this invention is the fact that it can be practiced without removing any existing insulation. FIG. 3 is a cross-sectional view of the cement liner 18 having the steel steampipe 20 arranged therein and in which portions of existing thermal insulation, which was provided at the time the steampipe was installed, remain in the annular space. That is, one portion 62 of previously installed insulation remains adhered to the inside of the cement conduit, another portion 64 of previously installed insulation remains adhered to the steel steampipe 20, and still a third portion 66 of previously installed insulation is represented as simply residing in that annular space and being caused to be captured in the new insulating foam 60 structure at the time such foam was installed.

FIGS. 4–12 illustrate the downward trend of condensate being discharged at three locations where performance tests were conducted. The results indicate that the average discharge rate was reduced by 300 pounds per hour at one location and by 100 pounds per hour at a second location.

EXAMPLE 1

Meter 1 (M1) was installed approximately in the middle of one 1000 foot section of test pipe. The amount of condensate being discharged at M1 at manhole 482 at Chestnut Street between 32nd and 33rd was measured every hour for one month prior to installation of the insulation. Then, in situ insulation of a 2000 feet test section of buried pipe was performed. The amount of condensate being discharged at M1 was measured every hour for one month after installation of the insulation. Before insulation the average discharge was 364 lbs/hr. After insulation the average discharge was 258 lbs/hr.

EXAMPLE 2

Meter 2 (M2) was installed approximately in the middle of another 1000 foot section of test pipe. The amount of consensate being discharged at M3 at manhole 187 at Broad & Wood in Philadelphia was measured every hour for one month prior to installation of the insulation. Then, in situ insulation of a 2000 feet test section of buried pipe was performed. The amount of condensate being discharged at M3 was measured every hour for one month after installation of the insulation. Before insulation the average discharge was 736 lbs/hr. After insulation the average discharge was 439 lbs/hr.

EXAMPLE 3

Meter 3 (M3) was installed down stream from the section of pipe being insulated. The amount of condensate being discharged at M2 at manhole 480 at Chestnut Street east of 34th in Philadelphia was measured every hour for one month prior to installation of the insulation. Then, in situ insulation of a 2000 feet test section of buried pipe was performed. The amount of condensate being discharged at M2 was measured every hour for one month after installation of the insulation. Before insulation the average discharge was 122 lbs/hr. After insulation the average discharge was 96 lbs/hr. These results show the effects of the insitu insulation of the 2000 foot section, on the next discharge point down stream.

TABLE 1

Typical Rigid Polyurethane Foam Formulation

| Ingredient | Parts |
| --- | --- |
| PMDI (polymethylene polyphenyl isocyanate) | 140 |
| polyol | 100 |
| fire retardant | 15 |
| catalyst | 2 |
| surfactant | 2 |
| FC-11 (fluorocarbon blowing agent) | 11 |

TABLE 2

Typical Rigid Polyisocyanurate Formulation

| Ingredient | Parts |
| --- | --- |
| PMDI | 134 |
| polyol | 20 |
| surfactant | 2 |
| FC-11 | 30 |

What is claimed is:

1. A method for the in-place insulation of an underground steam pipe within a conduit comprising the steps of:

forming a hole in the ground substantially aligned above the steam pipe within the conduit;

drilling an aperture in the conduit using a drill without affecting the steam pipe by monitoring a force being applied to the drill;

inserting tubing through the length of the formed hole so that a first end of the tubing passes through the drilled aperture and is positioned next to the steam pipe;

attaching a second end of the tubing to a pumping system;

pumping plastic foam through the tubing around the steam pipe using the pumping system;

withdrawing the tubing from the aperture and from the hole in the ground; and causing the foam to cure and become rigid thereby functioning as thermal insulation for the steam pipe.

2. The method of claim 1 further comprising selecting the tubing to be a fluorocarbon plastic.

3. The method of claim 1 further comprising creating the hole with a vacuum excavating device.

4. The method of claim 1 further comprising forming a plurality of spaced-apart holes in the ground, each substantially aligned above the steam pipe.

5. The method of claim 1 further comprising drilling a plurality of spaced-apart apertures in the conduit without affecting the steam pipe using the plurality of spaced-apart holes in the ground.

6. The method of claim 1 further comprising pumping the plastic foam, through the tubing, a distance of not more than 100 feet.

7. The method of claim 1 further comprising the steps of inserting a plastic liner into the hole and lowering a drill through the plastic liner prior to inserting the tubing.

8. The method of claim 1 further comprising selecting the plastic foam from the group of polyurethane, polyisocyanurate, and urethane-modified polyisocyanurate.

* * * * *